United States Patent [19]
Edelmann et al.

[11] 4,153,513
[45] May 8, 1979

[54] METHOD AND APPARATUS FOR THE CONTINUOUS DETERMINATION OF THE CONCENTRATION OF AN ENZYME SUBSTRATE

[75] Inventors: Hermann Edelmann, Tutzing-Unterzeismering; Peter Kraft; Karlheinz Mann, both of Weilheim; Peter Schuler, Munich; Alexander Hagen, Tutzing, all of Fed. Rep. of Germany

[73] Assignee: Boehringer Mannheim GmbH, Mannheim-Waldhof, Fed. Rep. of Germany

[21] Appl. No.: 826,008

[22] Filed: Aug. 19, 1977

[30] Foreign Application Priority Data

Sep. 20, 1976 [DE] Fed. Rep. of Germany ....... 2642232

[51] Int. Cl.² ............................................ G07N 31/14
[52] U.S. Cl. .............................. 195/103.5 R; 195/127; 195/139
[58] Field of Search ................ 195/103.5 R, 127, 139, 195/103.5 C, 103.5 U; 23/253 R, 253 A

[56] References Cited

U.S. PATENT DOCUMENTS

| | | | |
|---|---|---|---|
| 3,915,804 | 10/1975 | Messing | 195/103.5 U |
| 3,919,051 | 11/1975 | Koch et al. | 195/139 |
| 3,930,957 | 1/1976 | Cummings et al. | 195/103.5 R |
| 3,937,615 | 2/1976 | Clack et al. | 195/127 X |
| 4,067,777 | 1/1978 | Innerfield et al. | 195/103.5 R |

Primary Examiner—Thomas G. Wiseman
Attorney, Agent, or Firm—Sprung, Felfe, Horn, Lynch & Kramer

[57] ABSTRACT

Enzyme substrates in aqueous liquids are continuously measured by introducing a sample containing the substrate to be determined into a current of buffer solution, reacting the substrate on an immobilized enzyme and measuring, in a measurement chamber, a physical change in the solution brought about by the reaction, wherein a current of buffer solution containing the sample to be determined is passed alternatingly (i) directly through the measurement chamber with the production of a reference signal and (ii) first over the immobilized enzyme and thereafter through the measurement chamber with the production of a measurement signal, and relating the reference signal to the measurement signal to indicate the enzyme substrate initially present.

17 Claims, 5 Drawing Figures

METHOD AND APPARATUS FOR THE CONTINUOUS DETERMINATION OF THE CONCENTRATION OF AN ENZYME SUBSTRATE

The present invention relates to a method and apparatus for the continual determination of the concentration of an enzyme substrate in aqueous liquids.

The continuous determination of the concentration of certain substances creates problems which do not occur in individual analyses of the same sample. This is, for example, the case when, during the sample preparation or sample pretreatment in an individual analysis, kinetic processes can proceed until a final equilibrium is reached but which, in the case of continuous, direct sample feeding, only proceed incompletely or do not proceed to the end point or at least falsify the measurement result even when they can proceed to completion before the detector is reached. This problem arises, for example, in the determination of glucose in whole blood. In this determination, which employs the polarimetric measurement of oxygen consumption in the enzymatic oxidation of the glucose by glucose oxidase (GOD), false values can result due to the oxygen saturation of the hemoglobin. In the case of the determination of glucose in serum by this technique, however, this problem does not arise because the hemoglobin has been removed before the analytical sample preparation.

In the case of an individual determination of glucose in whole blood, it is also readily possible to saturate the hemoglobin with oxygen before the sample is introduced into the analytical system. The oxygen utilization which subsequently occurs can, just as in the case of the determination in serum, only be caused by the glucose. If, on the other hand, whole blood is continuously removed from the veins for monitoring the glucose, this is practically no longer possible. In such a case, the whole blood is, as a rule, passed through a dialyzer in which the glucose passes into the measurement cycle for the analysis, whereas the hemoglobin is held back. However, hemoglobin coming from the veins, which is impoverished in oxygen, will immediately take up oxygen as soon as it is able to do so. This occurs, in any case, in the dialyzer since an oxygen-saturated liquid is there present in the measurement cycle and diffusion of oxygen takes place within the dialyzer from the measurement cycle side to the sample cycle side. As a result of this, the liquid becomes impoverished in oxygen. A blocking of the hemoglobin or saturation thereof with oxygen, before it enters the dialyzer can scarcely be achieved economically because since, upon entry into the dialyzer, the concentration of the dissolved oxygen would also have to be the same as that in the buffer solution in the measurement cycle.

Problems similar to those discussed in the above illustrative case also arise in the case of numberous other determinations when they are carried out continuously. Theoretically, these problems can be overcome by using a second detector which measures the component of the system to be determined before the actual analytical reaction. However, in numerous cases, it is not feasible to provide two completely equal detectors. In spectral photometry an attempt has been made by a complicated arrangement, to direct the two light paths of a double-beam device as far as possible to one receiver, although photocells are easier to correlate than other measurement devices. The problem occurs especially in the case of ion-sensitive electrodes, oxygen electrodes and conductivity measurements, as well as generally in the case of all detectors which, in practice, cannot be reproduced with complete exactitude, i.e., where one detector always gives certain deviations in the indication from another one, even when great care is taken in the production thereof. However, even if this were possible, it would be of advantage to be able to avoid the expense required to achieve such exactitude of correlation.

This will now be explained in more detail, using an oxygen electrode as an example. The properties of such electrodes change with varying oxygen diffusion resistances of the membrane in front of the cathode. Thus, they are different from one covering to another and experience has shown that, merely due to this, changes of the signal height of up to 50% can occur. Further changes can occur due to blocking by impurities of the micropores of the polytetrafluoroethylene membrane. Furthermore, differences in the boundary layer conditions in front of the cathode, caused by onflow, play a part and thus production differences of the flowthrough chambers from one case to another or differing positionings of the electrodes in the chamber from one mounting to another. Finally, differences also occur in the linearity of the signals, of the zero current and of the gradient, as well as in the dynamic fluctuation behavior or of the transition characteristic to saturation. In addition, in the case of the arrangement of two detectors with separate amplifiers, differences between the amplifiers also increase the size of error.

It is an object of the present invention to overcome the above-described problems and to provide a simple method and apparatus which, without undue expense, permit the continuous monitoring of an enzyme substrate concentration.

The present invention provides a method for the continual determination of the concentration of an enzyme substrate in an aqueous liquid comprising introducing a sample containing the substrate to be determined into a current of buffer solution, permitting the substrate to react on an immobilized enzyme and physically measuring, in a measurement chamber, a change in the solution thereby brought about, wherein a current of buffer solution containing the sample to be determined is passed alternatingly (i) directly through the measurement chamber with production of a reference signal and (ii) first over the immobilized enzyme and thereafter through the measurement chamber, with the production of a measurement signal.

The process of the present invention can always be advantageously used when the measurement signal produced requires a base signal or a base signal line and the base signal line is not constant but rather fluctuates or drifts.

According to a preferred embodiment of the process, there is merely reversed, in regular intervals which are as short as possible, the sequence in which the sample-containing solution flows through the immobilized enzyme and the measurement chamber.

In the process according to the present invention, there is measured with the same measurement chamber (for example, an oxygen electrode or an ion-sensitive electrode, or conductivity measuring device), the actual concentration of the detection substance and, after contact with the immobilized enzyme, i.e., only chronologically displaced, the content of the detection substance as changed by the reaction, for example, there is measured the oxygen content before and after oxidation of blood sugar.

In comparison with known processes for the continuous determination of the concentration of a substance, by means of the present invention it is possible to continually obtain a base measurement line and thus also to exclude influences due to temperature changes, pressure changes or flow velocity changes. Thus, in regular time sequence, there is always available a base measurement line for reference setting. In the strict sense of the word, the process of the present invention does not represent a continuous determination of an enzyme substrate concentration but rather a continual but intermittent determination. As enzyme substrate, there is to be understood any substance which can be measured by an enzymatic analysis process.

The term "immobilized enzyme" is used here with its usual meaning. It includes carrier-bound enzymes, whether covalent or adsorptive, by incorporation, adhesion or polymerizing in, or by cross-linking of immobilized enzymes or the like. The immobilized enzyme can be in the form of a powder, granulate or the like and can be bound to membranes, fibers or surfaces of formed bodies. Two preferred manners of use of the immobilized enzyme consist in the arrangement of a column filled with a granulated, enzymatically active material in the current of a buffer solution or in the arrangement of an enzyme stretch, i.e., of a tube, the inner surface of which is enzymatically-active. In the latter case, there can be used, for example, synthetic resin tubes or pipes which consist, for example, of a polyamide with an enzyme immobilized on the surface thereof by covalent bonding or adhesion.

The samples for which the method of the present invention can be employed include, for example, physiological fluids, such as whole blood or urine or process solutions. Therefore, the method is especially suited for monitoring body functions and the composition of process streams, e.g., of nutrient solutions for micro-organisms and the like.

The sample containing the substrate to be determined is preferably introduced continuously into the flowing buffer solution. However, it is also possible to provide an intermittent introduction in which the volumes of sample move block-like in the current of buffer solution. A device suitable for this is known, for example from German Patent Specification No. 2,130,308. A circulating buffer solution is preferably used when regeneration thereof is possible and/or when accumulating substances are tolerable.

In the case of the preferred continuous introduction of the sample, this is preferably brought into contact with the current of buffer solution via a dialysis membrane so that the substance to be monitored can be dialyzed into the buffer solution. In this way, nondialyzable substances, which could cause disturbances upon contact with the enzyme or in the measurement chamber, are excluded. However, if desired, the sample to be determined can be introduced directly into the current of buffer solution. In the latter case, it is preferable to previously dilute the sample by the addition of buffer solution, heparin solution or the like in such a manner that no disturbances can occur due to suspended solid materials upon contact with the immobilized enzyme or in the measurement chamber and that the concentration of the substance to be determined is brought within the measurement range of the detector. Disturbances due to blocking of the immobilized enzyme can be avoided by choosing a cross-section which is as open as possible, for example, an enzyme stretch in the form of a tube with an enzymatically active surface. Predilution is preferably carried out by first inroducing the sample into a branch current of buffer solution which is then mixed with the main current of the buffer.

The sample-containing buffer solution can be allowed to flow through the measurement chamber until a constant reference signal or measurement signal is obtained before again changing over but this is not necessary. The enzyme reaction also need not run to completion, i.e. substrate can still be present after passage through the immobilized enzyme. In the case of a circulating buffer solution, unreacted substrate can be completely removed in a later reaction by means of further immobilized enzyme. Other substances in the buffer solution which might have a disturbing influence after passage through the measurement chamber in the case of renewed measurement are preferably converted into nondisturbing substances or are removed therefrom. This can be accomplished, for example, by further contacting with an appropriate immobilized enzyme. An especially preferred embodiment of the process is the above-mentioned reversal of the sequence, in which passage takes place through the enzyme and the measurement chamber, in which the sample solution, without previous contact with the immobilized enzyme, passes directly into the measurement chamber and, therefore, still contains the total enzyme substrate, and is subsequently brought into contact with the immobilized enzyme and is thereby removed. If, however, conditions are selected which do not lead to the complete reaction of the substrate, for example of the glucose, then, in this case, further contacting with immobilized enzyme is carried out.

If, in the enzymatic reaction, substances are formed which influence the measurement reaction or are included by it, they are preferably again removed from the buffer solution, for example by means of adsorption agents and/or ion exchangers. This is, for example, the case with conductivity measurements. However, the process of the present invention also makes it possible to operate without such removal of disturbing substances in the cycle since, of course, in each cycle, a new base measurement signal is produced which serves as a reference point for the substrate measurement signal and thus excludes an influence of the accumulation of disturbing substances on the determination itself.

The time of a process cycle, i.e. the changeover from one cycle to the next one, depends upon the flow velocity of the buffer solution, the length of the stretches through which flowing takes place, the time constant of the detector and the velocity of the enzyme reaction. In practice, the period of time from one changeover to the next is between a few minutes and a few seconds. In the case of a changeover time of 15 seconds, a base-reference signal, i.e. a measurement signal, would be obtained every 30 seconds. For example, in the case of an oxygen electrode, a certain period of time is needed in order to adjust the diffusion equilibrium.

The device according to the present invention will now be described with reference to the accompanying drawings, in which.

Figure 5:
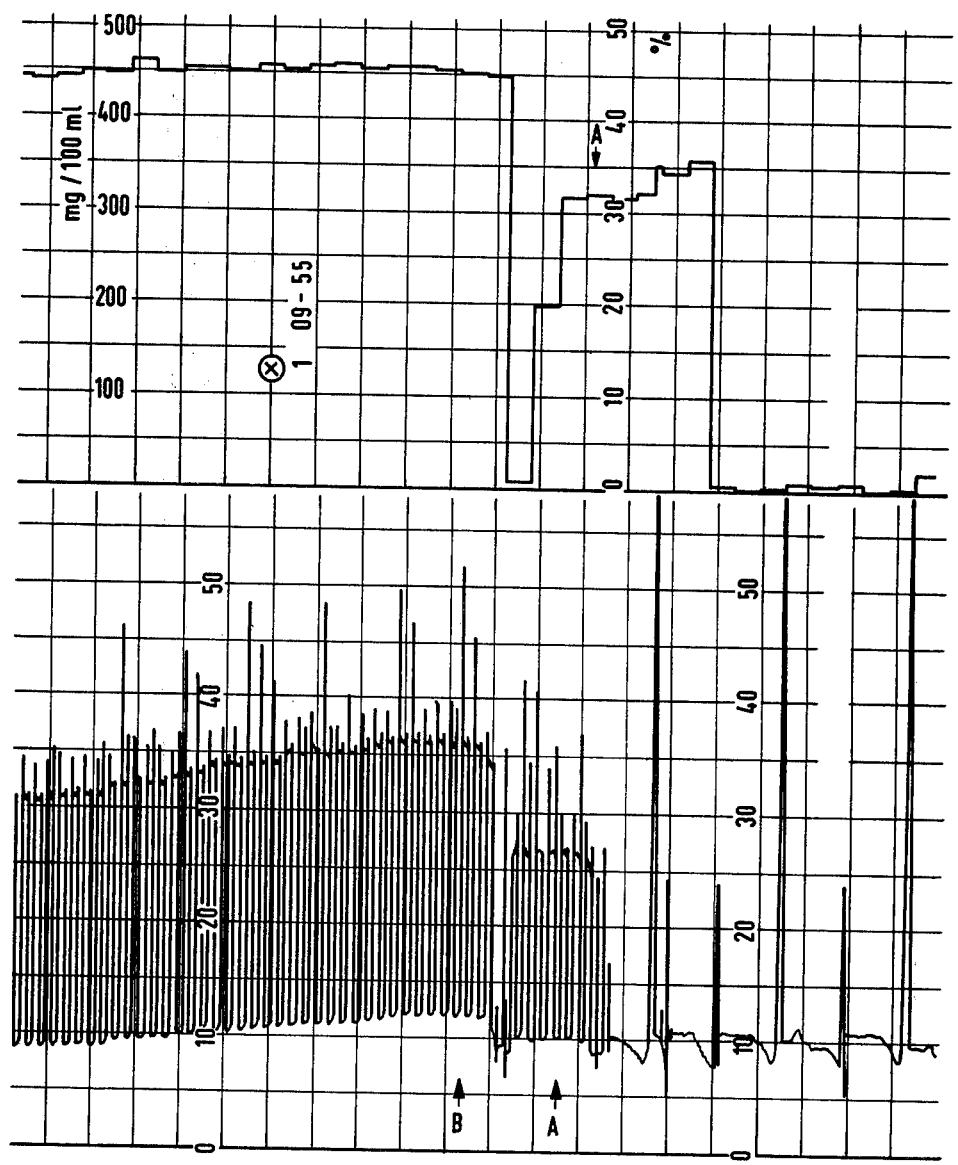

FIG. 5 a typical measurement curve which has been recorded with a device according to the present invention.

The apparatus of the invention for carrying out the above-described new method comprises, in general, a buffer reservoir 1, a sample introduction device 2, an immobilized enzyme 3 and a measurement chamber 4, which are connected together in this sequence by tubes to give a circulatory system, and also comprises a bridging tube 5 between the sample introduction device 2 and the measurement chamber 4 and a changeover valve 6 which alternatingly closes the bridging tube 5.

Figure 1:
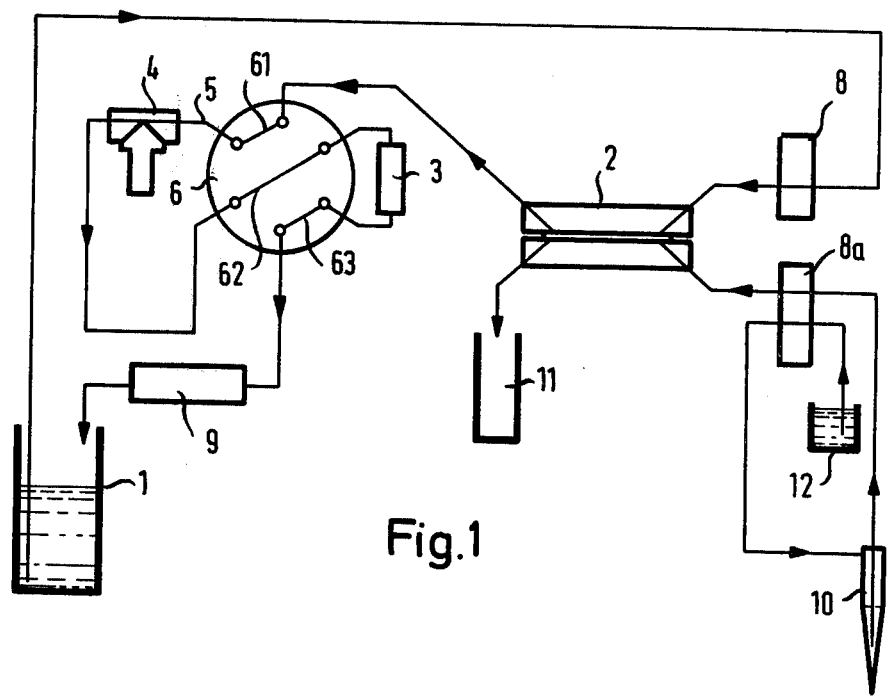
FIG. 1 is a schematic representation of a device according to the present invention in a first switch position.

The embodiment illustrated in FIG. 1 comprises a changeover valve 6 with three channels (61, 62, 63). In a first position of the changeover valve, the first channel 61 forms the bridging tube 5, the second channel 62 conducts the flow-off from the measurement chamber 4 to the immobilized enzyme 3 and the third channel 63 connects the flow-off from the immobilized enzyme 3 with a pipe leading to the container 1.

Figure 2:
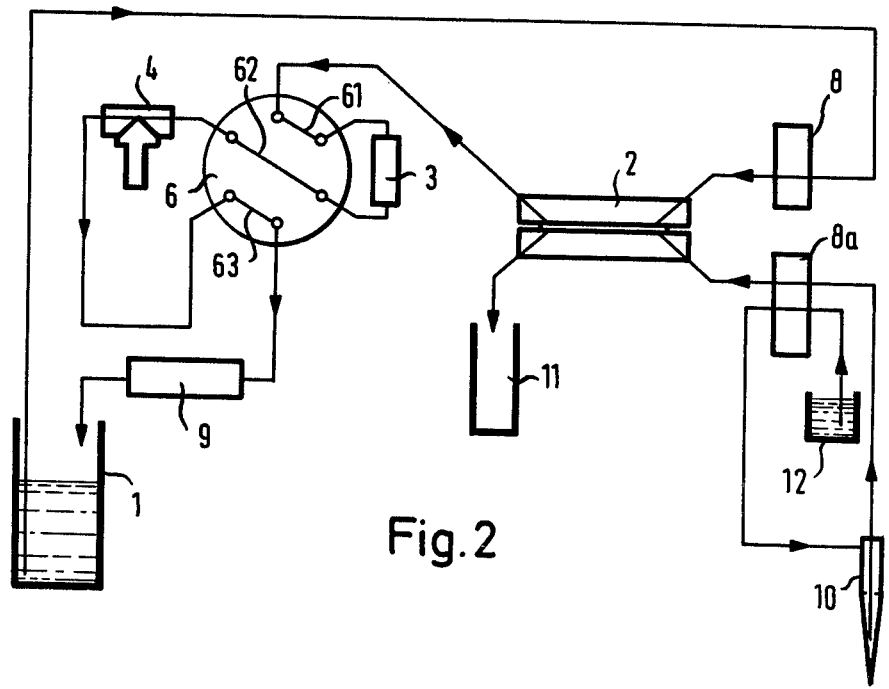
FIG. 2 is the device of FIG. 1 in another switch position.

The second position of the changeover valve 6 of FIG. 1 is illustrated in FIG. 2. In this case, the first channel 61 leads to the enzyme 3, the second channel connects the flow-off from the immobilized enzyme 3 with the measurement chamber 4 and the third channel 63 connects the flow-off from the measurement chamber 4 with a pipe leading to the container 1. In the embodiment illustrated in FIGS. 1 and 2, the device also comprises two pumps 8, 8a which maintain the flow in the measurement cycle and in the sample circulation, a reactor 9 for the conversion of remaining substrate, a vein canula 10 with which whole blood is passed via the pump 8a into the sample introduction device 2, which is constructed as a dialyzer, and further to a collection vessel 11 and a container 12 for a heparin dilution solution which, mixed with the whole blood taken up by the canula 10 is passed to the dialyzer 2.

Figure 3:
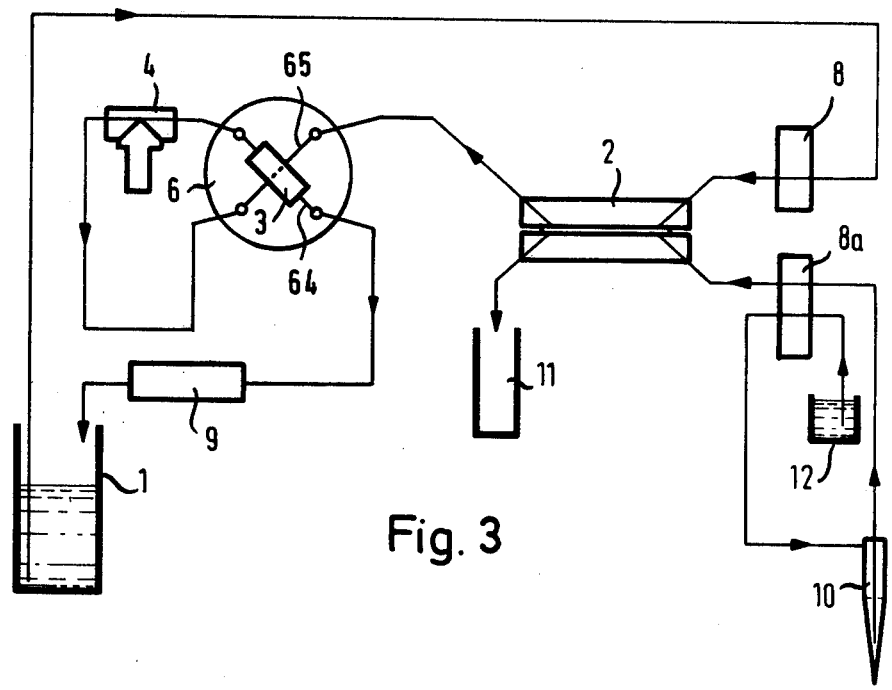
FIG. 3 is another embodimental form of a device according to the present invention in a first switch position.
Figure 4:
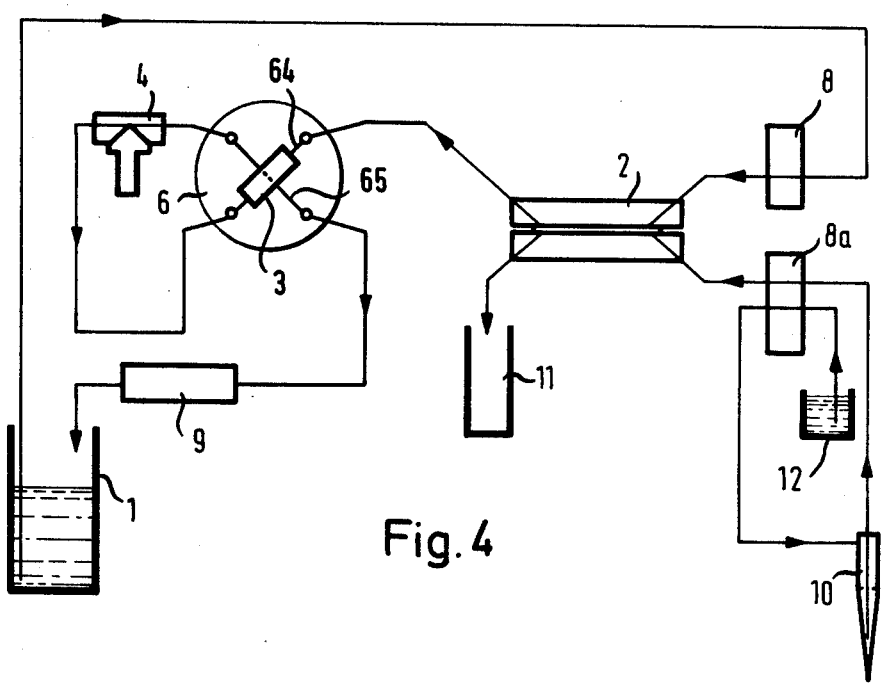
FIG. 4 is another switch position of the device of FIG. 3.

Another embodiment of the present invention is illustrated in FIGS. 3 and 4, this embodiment permitting a shortening of the switchover times. Whereas the device as a whole corresponds substantially to that described in FIGS. 1 and 2, there is here provided a changeover valve 6 with two channels (64, 65), the first channel 64 containing the immobilized enzyme 3. In a first position of the changeover valve, the first channel 64 connects the flow off from the measurement chamber 4 with a pipe leading to the container 1 and the second channel 65 forms the bridging tube 5.

In the position of the changeover valve illustrated in FIG. 4, the first channel 64 connects the flow off from the sample introduction device 2 with the measurement chamber 4 and the second channel 65 connects the flow off from the measurement chamber 4 with a pipe leading to the container 1.

In the operation of the device according to the present invention, blood is taken off through the vein canula 10 and simultaneously diluted in a predetermined volume ratio with a heparin solution supplied from the storage container 12 by the pump 8a. The mixture thus obtained of whole blood and heparin solution is aspirated by the pump 8a and passed to the sample introduction device 2 which is constructed as a dialyzer, and further passed from there into the collection container 11. In the dialyzer, the mixture of whole blood and heparin solution is in exchange relationship with buffer solution supplied by the pump 8 from the storage container 1. The dialyzable low molecular weight substances, for example glucose, hereby pass over from the diluted whole blood into the measurement cycle and pass into the channel 61 or 64 of the changeover valve 6. In the position of the changeover valve illustrated in FIGS. 1 and 2, this channel forms a part of the bridging tube 5 and the sample-containing buffer solution passes, therefore, directly into the measurement chamber 4 with the production of a corresponding measurement signal, which is indicated by an appropriate device (not shown). Thereafter, the current of buffer solution returns to the changeover valve in channel 62 comes into contact with the immobilized enzyme 3 and then flows back into the changeover valve and through channel 63 via the reactor 9 into the buffer storage vessel 1. In the case of the embodiment of FIGS. 3 and 4, the enzyme stretch is in the channel 64 but otherwise the method of operation is precisely as described above.

Between the sample introduction device 2 and the changeover valve 6 there can, if desired, also be arranged a flow reversal valve with which, if necessary, gas bubbles or simular disturbances can be quickly removed from the cycle. This flow reversal valve is then preferably so arranged that, before reaching the container 1 flow takes place through the reactor 9.

An especially advantageous use of the process and of the device according to the present invention is for the control of the addition of substances in dependence upon the determined measurement values. For example, with the above-described embodiment of the present invention in which the blood sugar concentration is measured, in dependence upon the measurement value obtained, a blood sugar lowering agent, such as insulin, or a blood sugar increasing substance can be administered. In an analogous manner, it is possible, upon the basis of the measurement values, when these are used for monitoring reactions which are taking place, to control, inter alia, the addition of starting materials for these reactions.

The following Examples are given for the purpose of illustrating the present invention:

EXAMPLE 1

There is employed the device illustrated in FIGS. 1 and 2. A commercially available vein canula 10, which permits a direct heparinization of the blood upon its tip, takes off the blood. For this purpose, the peristaltic pump 8a feeds a heparin solution from a storage vessel 12 at a rate of 5 ml. of heparin solution (50,000 U/100 ml.) per hour to the canula. The second tube inserted into the pump 8a aspires from the canula a mixture of 5 ml. heparin solution per hour and 5 ml. of blood per hour. This mixture now passes to the primary side of the sample introduction device 4, which is constructed as a dialyzer and from there to a waste vessel 11. During the residence time in the dialyzer, the heparinized blood enters into exchange with the buffer flowing through the secondary side of the dialyzer. The running stretch in the dialyzer has a length of 15 cm. The buffer (0.2M phosphate buffer pH 6.0, containing 0.02% alkali acid) is taken by the peristaltic pump 8 from a 5 liter capacity storage vessel 1, through which air is bubbled in order continuously to saturate the buffer with oxygen. The whole arrangement is thermostatically controlled at 30° C.

From the supply side of the peristaltic pump 8, the buffer passes to the secondary side of the dialyzer. It is there brought to about 1% of the glucose concentration of the heparinized blood. As described in connection with FIGS. 1 and 2, the glucose-containing buffer flows alternatingly, on the one hand, through the measurement chamber 4 and then through the immobilized enzyme 3 (FIG. 1) and, on the other hand, through the immobilized enzyme 3 and then through the measurement chamber 4 (FIG. 2). The enzyme reactor 3 and also the enzyme reactor 9 both contain immobilized glucose oxidase (GOD).

The measurement currents produced in the measurement chamber 4 are transmitted via an amplifier to an indicating device. FIG. 5 shows a typical recording of the results obtained. The lower turning point of the curve corresponds to the base measurement signal and the upper turning point to the substrate measurement signal. A indicates the calibration at which a blood sugar standard of 320 mg./100 ml. was employed and B indicates the switch-over to the sample taken from a vein. The recognizable base line increase, which is due to hemoglobin would falsify the glucose signal by about 40 mg./100 ml. if it were not corrected by the inversion arrangement according to the present invention.

EXAMPLE 2

There is used the device illustrated in FIGS. 3 and 4. The two enzyme stretches 3 and 9 contain immobilized urease and the measurement chamber 4 is constructed for the measurement of conductivity. When passing over a urea-containing buffer solution, the urea is converted by the urease into ammonia and carbonic acid. These products alter the conductivity of the buffer and can, therefore, in this way be determined directly. The buffer solution consists of $7 \times 10^{-3}$M 2-[4-(2-hydroxyethyl)-piperazin-1-yl]-ethane-sulphonic acid, adjusted with 0.2M trimethylolaminomethane to pH 7.4. The base conductivity of this buffer is about 150 micro-siemens. In the case of dialysis in the sample introduction device 2, the conductivity of the buffer increases, due to electrolytes which have passed over, by about 200 micro-siemens. Depending upon the urea content, the urea decomposition products produced by the enzyme 3 provide a further 50 to 200 micro-siemens.

The conductivity cell measures linearly from 5 to about 15,000 micro-siemens. Therefore, the buffer can be reused until the base conductivity approaches 15,000 micro-siemens and is then replaced by fresh buffer.

Alternatively, an ion exchange bed can be provided in the reactor 9, which removes the ions formed. Instead of this, the reactor can also contain an electrodialysis unit, an ion exchange membrane or another appropriate means for the removal of the ions which increase the conductivity.

It will be understood that the specification and examples are illustrative but not limitative of the present invention and that other embodiments within the spirit and scope of the invention will suggest themselves to those skilled in the art.

What is claimed is:

1. Method for the continuous determination of the concentration of an enzyme substrate in an aqueous liquid which comprises introducing a sample containing the substrate to be determined into a current of flowing buffer solution, reacting the substrate contained in said buffer solution with an immobilized enzyme and measuring a physical change in the solution brought about by said reaction using a single measurement chamber, by passing the buffer solution containing the sample to be determined in an alternating manner (i) directly through the measurement chamber thereby producing a first measurement signal and (ii) then over said immobilized enzyme and thereafter through said measurement chamber thereby producing a second measurement signal and comparing the signals to determine the concentration of the substrate.

2. A method as claimed in claim 1 wherein the sample containing the substrate to be determined is introduced continuously into the current of flowing buffer solution.

3. Method as claimed in claim 1 wherein the sample containing the substrate to be determined is dialyzed into the current of flowing buffer solution.

4. Method as claimed in claim 1 wherein the sample to be determined is introduced directly into the current of flowing buffer solution.

5. Method as claimed in claim 1 wherein the current of flowing buffer solution containing the sample is allowed to flow through said measurement chamber until a constant base signal or measurement signal is obtained and thereafter said solution is passed to the alternate route (i) or (ii).

6. Method as claimed in claim 1 wherein interfering components of the sample contained in the current of flowing buffer solution are changed to render them non-interfering or removed therefrom.

7. Method as claimed in claim 6 wherein the current of flowing buffer solution containing the sample, after passing the measurement chamber, is contacted with an immobilized enzyme until the substrate contained in said solution is completely reacted.

8. Method as claimed in claim 6 wherein the current of flowing buffer solution containing the sample is contacted with an adsorption agent, or an ion exchanger, for the removal of any interfering components from the current of flowing buffer solution containing the sample.

9. Method as claimed in claim 4 wherein the sample to be determined is prediluted with a buffer solution and is then introduced into the current of flowing buffer solution.

10. Method as claimed in claim 1 wherein said sample is a protein containing sample and is first diluted with a heparin solution before being introduced into the current of flowing buffer solution.

11. Method as claimed in claim 10 wherein said diluted solution is dialyzed into the current of flowing buffer solution.

12. Apparatus for conducting the method as claimed in claim 1 which apparatus comprises a buffer storage container communicating with a sample introduction device, a sample inlet stream also communicating with said sample introduction device, said device being capable of mixing the sample and buffer and communicating with a bridging channel to a chamber holding immobilized enzyme and with a bridging channel to a measurement chamber, and a changeover valve therein adapted to alternatingly open and close said bridging channels to permit alternating communication between said sample introduction device and (i) the immobilized enzyme chamber and (ii) the measurement chamber.

13. Apparatus as claimed in claim 12 wherein the changeover valve comprises three channels in which, in a first position of the changeover valve, the first channel forms the bridging tube, the second channel passes the flow from the measurement chamber to the immobilized enzyme and the third channel connects the flow from the immobilized enzyme with a pipe leading to the buffer storage container and, in a second position of the changeover valve, the first channel forms the pipe to the immobilized enzyme, the second channel connects the flow from the immobilized enzyme with the measurement chamber and the third channel connects the flow from the measurement chamber with the pipe leading to the buffer storage container.

14. Apparatus as claimed in claim 12 wherein the changeover valve has two channels, the first of which contains an immobilized enzyme, in which, in a first position of the changeover valve, the first channel connects the flow from the measurement chamber with a pipe leading to the buffer storage container and the second channel forms the bridging pipe and, in a second position of the changeover valve, the first channel connects the flow from the same introduction device with the measurement chamber and the second channel connects the flow from the measurement chamber with the pipe leading to the buffer storage container.

15. Apparatus as claimed in claim 12 additionally comprising a reactor for the removal or conversion of interfering components arranged in the conduit leading to the buffer storage container.

16. Apparatus as claimed in claim 15 wherein said reactor contains the same immobilized enzyme as said immobilized enzyme chamber.

17. Apparatus as claimed in claim 12 additionally comprising an injection device and wherein the measurement chamber generates a measurement signal which controls the introduction of a certain amount of an injection liquid into the liquid in which the enzyme substrate concentration is determined.

* * * * *